(12) United States Patent
Nyholm et al.

(10) Patent No.: US 9,895,120 B2
(45) Date of Patent: Feb. 20, 2018

(54) TRACKING A MOTION OF A JAW

(71) Applicant: PLANMECA OY, Helsinki (FI)

(72) Inventors: Kustaa Nyholm, Siuntio (FI); Lasse Toimela, Helsinki (FI)

(73) Assignee: PLANMECA OY, Helsinki (FI)

( * ) Notice: Subject to any disclaimer, the term of this patent is extended or adjusted under 35 U.S.C. 154(b) by 154 days.

(21) Appl. No.: 15/065,249

(22) Filed: Mar. 9, 2016

(65) Prior Publication Data

US 2016/0262711 A1    Sep. 15, 2016

Related U.S. Application Data

(60) Provisional application No. 62/130,447, filed on Mar. 9, 2015.

(51) Int. Cl.
| | | |
|---|---|---|
| A61B 6/03 | (2006.01) | |
| A61B 5/11 | (2006.01) | |
| A61B 6/14 | (2006.01) | |
| A61B 6/00 | (2006.01) | |
| A61B 6/12 | (2006.01) | |
| A61B 5/00 | (2006.01) | |

(52) U.S. Cl.
CPC ............ *A61B 6/501* (2013.01); *A61B 5/0035* (2013.01); *A61B 5/1114* (2013.01); *A61B 5/1127* (2013.01); *A61B 6/032* (2013.01); *A61B 6/12* (2013.01); *A61B 6/14* (2013.01); *A61B 6/4417* (2013.01); *A61B 5/0077* (2013.01); *A61B 5/4542* (2013.01); *A61B 6/461* (2013.01)

(58) Field of Classification Search
CPC ... A61B 5/0035; A61B 5/0077; A61B 5/1114; A61B 5/1127; A61B 5/4542; A61B 6/032; A61B 6/12; A61B 6/14; A61B 6/4417; A61B 6/461; A61B 6/501
See application file for complete search history.

(56) References Cited

U.S. PATENT DOCUMENTS

| | | | |
|---|---|---|---|
| 4,836,778 A | 6/1989 | Baumrind et al. | |
| 4,859,181 A | 8/1989 | Neumeyer | |
| 7,182,737 B2 * | 2/2007 | Kim | A61C 19/045 600/587 |
| 2008/0311537 A1 | 12/2008 | Minagi et al. | |
| 2011/0218426 A1 | 9/2011 | Shinjo et al. | |
| 2013/0157218 A1 | 6/2013 | Brunner et al. | |
| 2015/0132715 A1 | 5/2015 | Yeh et al. | |

FOREIGN PATENT DOCUMENTS

| | | |
|---|---|---|
| DE | 102012104912 A1 | 11/2013 |
| JP | H08117214 A | 5/1996 |
| JP | 2001112743 A | 4/2001 |
| JP | 2013192695 A | 9/2013 |

* cited by examiner

*Primary Examiner* — Mark R Gaworecki
(74) *Attorney, Agent, or Firm* — Fay Sharpe LLP

(57) ABSTRACT

The invention relates to tracking motion of a patient's jaw, wherein motion of a tracking item which represents motion of the jaw is followed by at least one camera arranged to a medical x-ray imaging apparatus and wherein the motion detected by the at least one camera is applied on a digital model depicting hard tissue of the jaw. The moving digital model of the hard tissue of the jaw thus generated is shown on a display to visualize movement of the hard tissue.

19 Claims, 5 Drawing Sheets

TRACKING A MOTION OF A JAW

The application claims the benefit of U.S. Provisional Application Ser. No. 62/130,447 filed Mar. 9, 2015, the disclosure of which is herein incorporated by reference.

FIELD OF INVENTION

The invention relates to arrangements and methods for tracking and generating a digital model visualizing motion of hard tissue of a person's jaw.

BACKGROUND OF INVENTION

Various systems such as ones employing mechanical, electronic, ultrasonic, electromagnetic and optical techniques have been used in connection with recording movements of a human jaw. One typical solution includes attaching physical markers to both maxilla and mandible and recoding their respective relative motion. Such systems are known to include visualization of the measured or detected movement on a display, possibly as applied to e.g. a digital surface model of cranial hard tissue.

Regardless the technology, the work-flow involved in these procedures is often time-consuming and laborious as it may include using separate apparatus and operations performed individually and separate from each other. These operations may include attaching markers to the anatomy, generating jaw movements and detecting and recording the movements of the markers, and generating a model visualizing the jaw movements which may then be shown on a display. For one, in case modelling of the jaw movements is visualized as a separate process afterwards and it is only then realized that additional movement information would be needed or be desirable, to enhance the digital motion model, this will not be possible until the next time one will be able to harness the patient with the markers and detect and record the jaw movements anew.

Examples of the prior art to track jaw motions include systems described in patent publications U.S. Pat. Nos. 4,836,778, 4,859,181, US 2013/0157218 and WO 2013/0175018.

BRIEF DESCRIPTION OF INVENTION

The invention and its preferable embodiments include an arrangement and method in which a digital model showing a person's jaw motions is generated in the context of a medical x-ray imaging apparatus, such as CT apparatus arranged to acquire image information for generating surface models of cranial hard tissue anatomies. This enables acquiring both x-ray image data and jaw motion data with the same apparatus. By equipping the arrangement with image processing means and a display on which a modelled motion of the hard tissue can be visualized in the same context in which photographing the motion of reference objects attached to a cranial anatomy is carried out, embodiments of the invention enable following the movements of the hard tissue in real time while the patient is present to generate any desired chewing or other jaw motion to be modelled.

According to one embodiment, the method according to the invention includes providing at least one camera arranged in physical connection with a CT imaging apparatus. The method includes attaching a first tracking item to a person's jaw and attaching a second tracking item to a person's upper jaw or to a part of the person's anatomy which is in a stationary connection with the upper jaw. A CT reconstruction of hard tissue of anatomy of the person is generated and locations of the tracking items relative to the hard tissue anatomy are identified. In one embodiment, a series of images of the tracking items using the at least one camera are captured while the patient is performing a jaw motion and locations of the tracking items in the images are determined. The poses of the hard tissue anatomy are then resolved using knowledge of a relationship between the tracking items and the anatomy. The poses of the hard tissue anatomies can be transferred to a visual system to display the digital model chewing motion of the jaw.

BRIEF DESCRIPTION OF FIGURES

The following Figs. are used to present some aspects of various embodiments of the invention.

DETAILED DESCRIPTION OF INVENTION

Figure 1:
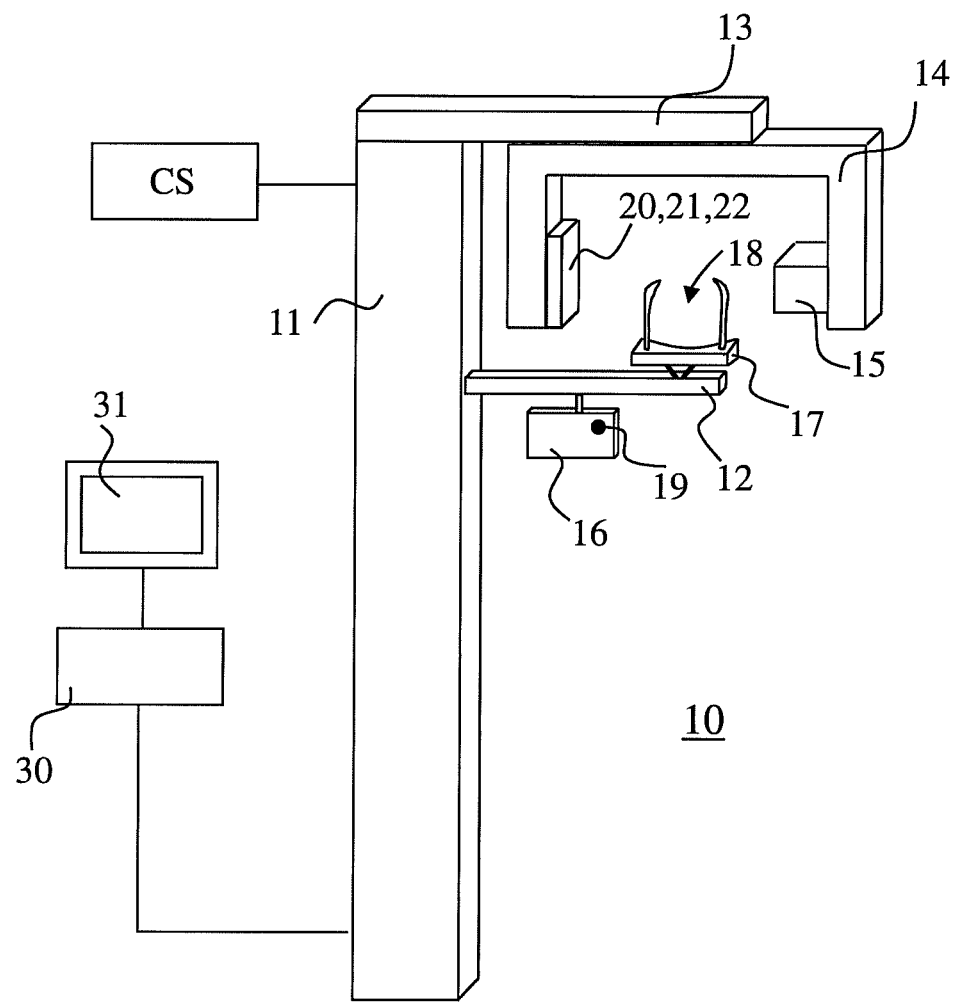
FIG. 1 shows basic parts of one preferable arrangement according to the invention.

FIG. 1 shows basic parts of one preferable arrangement according to the invention. The arrangement of FIG. 1 includes a medical x-ray imaging apparatus (10) comprising a vertical support construction (11) from which horizontally extends an arm (12) supporting a patient support means (17) and an arm part (13) which supports an arm part (14) supporting imaging means of the apparatus. The arm part (14) supporting the imaging means is arranged rotatable. The imaging means of the apparatus include an x-ray source (15) and a receiver of x-ray image information (21) arranged at a distance from each other. The imaging means are located with respect to the patient support means (17) such that an imaging station (18) is created within an area between the x-ray source (15) and the receiver of x-ray image information (21) such that a beam generated by the x-ray source (15) can be directed through said imaging station (18) towards the receiver of x-ray image information (21). The apparatus includes control means of which FIG. 1 shows a user interface (16) arranged to the arm (12) supporting a patient support means (17) and an operation mode selection means (19) pertaining in it. In the apparatus according to FIG. 1, the receiver of x-ray image information (21) is arranged as part of a receiver module of image information (20), a detector module which is arranged in an operational connection with a computer (30). A means for processing image information is arranged to the computer (30) and the computer which is also arranged in an operational connection with a display (31). The user interface (16) may be equipped with a display, too, and there may be a display arranged to some other structure of the x-ray imaging apparatus as well. Physical components and subsystems of the control system (CS) may be arranged at various places of the arrangement, some may be included in the computer (30) and some be arranged e.g. in the vertical support construction (11) or in the proximity or integrated with the component of the arrangement to be controlled.

Figure 2:
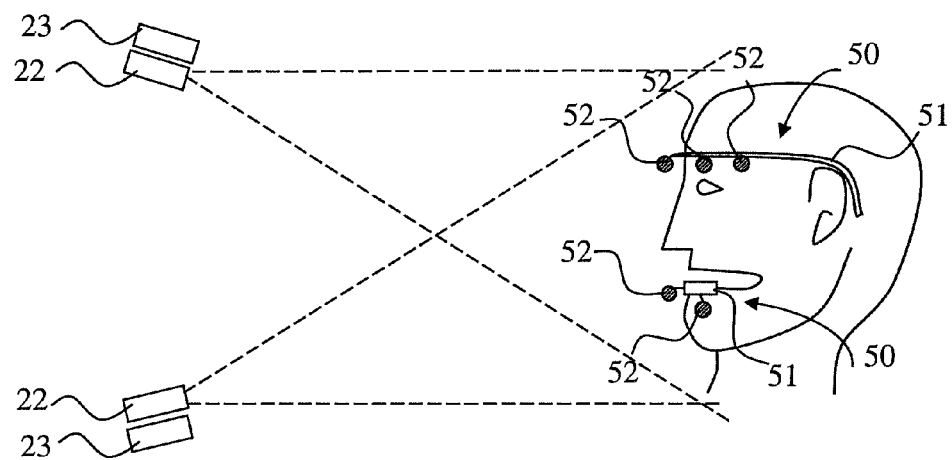
FIG. 2 shows a principled arrangement for detecting jaw motion according one system applicable for use in the context of the invention.

FIG. 2 shows a principled arrangement of detecting jaw motion according to one system applicable for use in the context of the invention. The arrangement includes two cameras (22) arranged at a distance from each other and aimed to photograph a person's head whereto tracking means (50) are connected. In the arrangement according to FIG. 2, the tracking means (50) consist of two separate support constructions (51) for reference objects such as light reflecting objects (52). One of the support constructions (51) is connected to a person's forehead, another to a person's lower jaw. The arrangement of FIG. 2 also includes light sources (23) arranged at close proximity of the cameras (22). The light source (23) is arranged to emit light essentially in a direction at which the proximate camera (22) is aimed.

Figure 3:
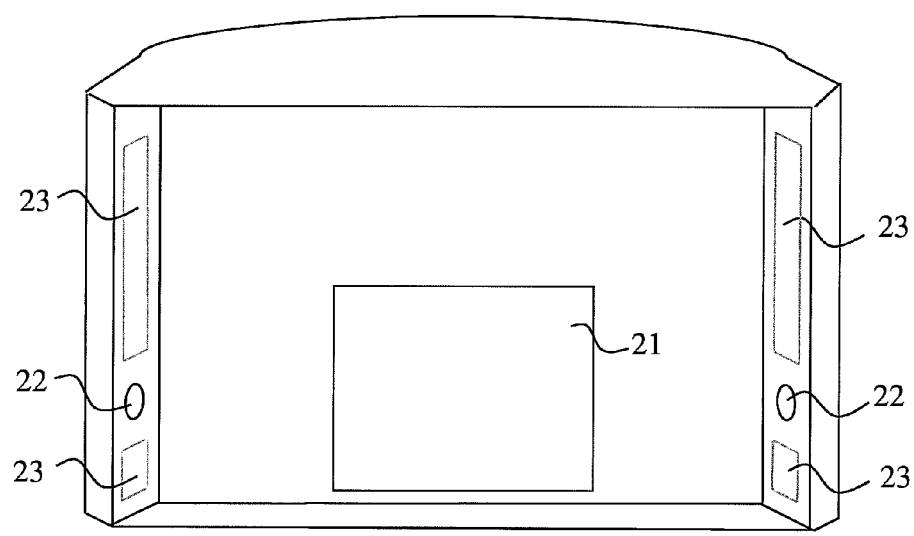
FIG. 3 shows a detector module attachable to a medical x-ray apparatus including components applicable for use in the context of the invention.

FIG. 3 shows a detector module (20) attachable to a medical x-ray apparatus including components applicable for use in the context of the invention. Contrary to what has been presented in FIG. 2, the cameras (22) are arranged to the module (20) not at a vertical but at a horizontal distance from each other, and there are light sources (23) above and below the cameras (22). An x-ray image detector (21) is also arranged in the module. Attaching of the module (20) to the medical x-ray apparatus is to be realized such that the x-ray image detector (21) is or can be aligned at the imaging station (18) of the apparatus.

Figure 4:
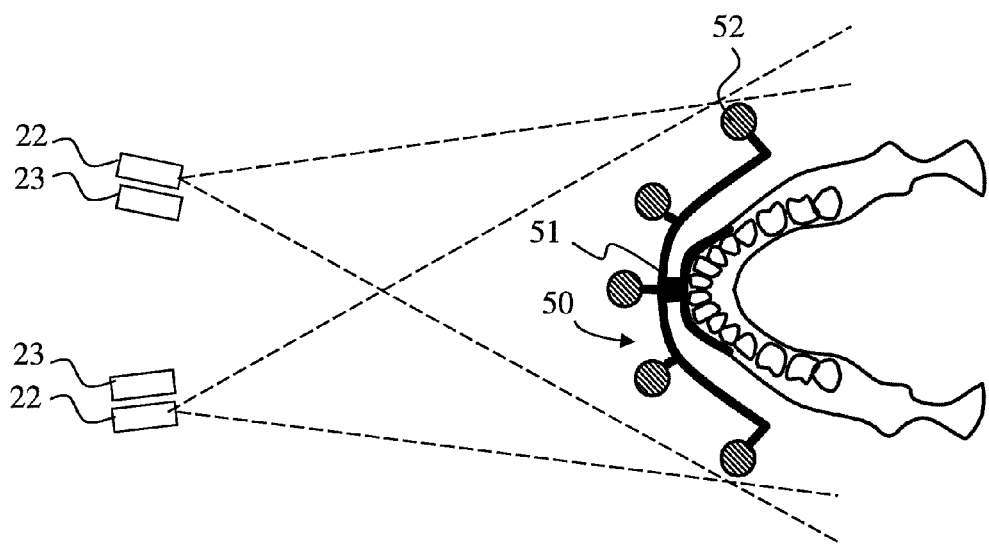
FIG. 4 shows an arrangement for motion tracking imaging in which a tracking device is attached to a mandible, in the field of view of two cameras.

FIG. 4 shows an arrangement for motion tracking imaging in which a tracking means is attached to a mandible and in the field of view of two cameras. The tracking means (50) of FIG. 4 comprises a support structure (51) for five light-reflecting reference objects (52). The two cameras (22) of the arrangement are located and aimed such with respect to the light-reflecting reference objects (52) that all five of them are in the line of sight of both of the cameras (22). The arrangement includes a light source (23) at close proximity of both of the cameras (22), the light sources (23) being arranged to emit light essentially in a direction at which the proximate camera (22) is aimed.

Figure 5:
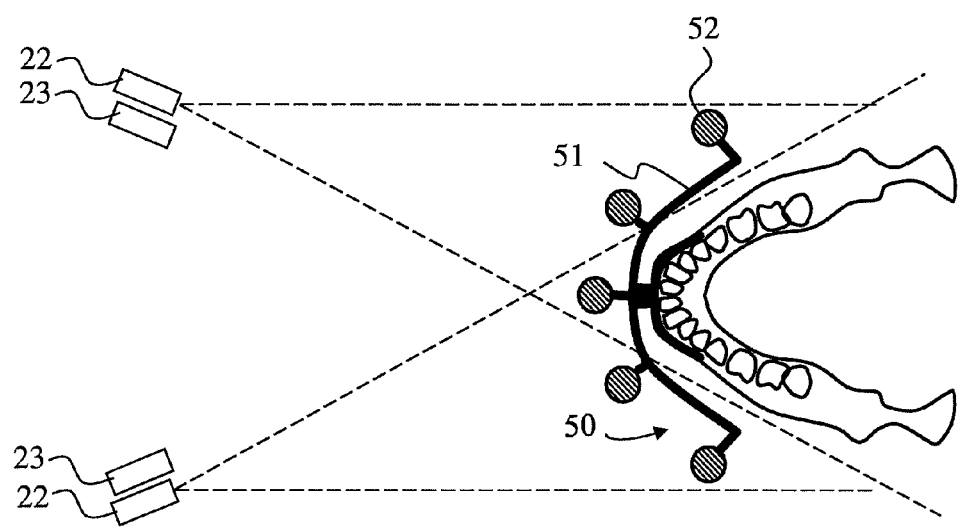
FIG. 5 shows an arrangement for motion tracking imaging as in FIG. 4 but in which only a portion of reference objects of the tracking device are in the field of view of either of two cameras.

FIG. 5 shows an arrangement for motion tracking imaging as in FIG. 4 but in which the cameras (22) are located at a longer distance from each other. Such arrangement may be applied e.g. in the context like the one shown in FIG. 3, in which the cameras (22) are located on opposite sides of the x-ray image detector (21) of the detector module (20).

In the arrangement of FIG. 5, only a portion of the reference objects (52) of the tracking means (50) are in the field of view of either of the two cameras (22), but resolving the pose of the tracking means (50) is possible also in the context of such arrangement, as long as at least one of the reference objects (52) is in the field of view of both cameras (22). Such procedure may comprise resolving, first, the three dimensional position of one reference object (52) in the field of view of both cameras. This can be done by e.g. triangulating the position using the camera calibration information and detected locations of the reference objects (52), after which a corresponding point in a tracking device model is translated into the resolved position. The tracking device model is then rotated about this point so that when projected into both camera views, the squared distance between the projected point position and the corresponding detected reference object position is minimized. The rotation and the translation define the pose of the tracking model.

The arrangements for acquiring information for generating a digital model showing motion of a cranial hard tissue anatomy discussed above are based on using two cameras, but the invention can be implemented using arrangements based on using any number of cameras.

Figure 6:
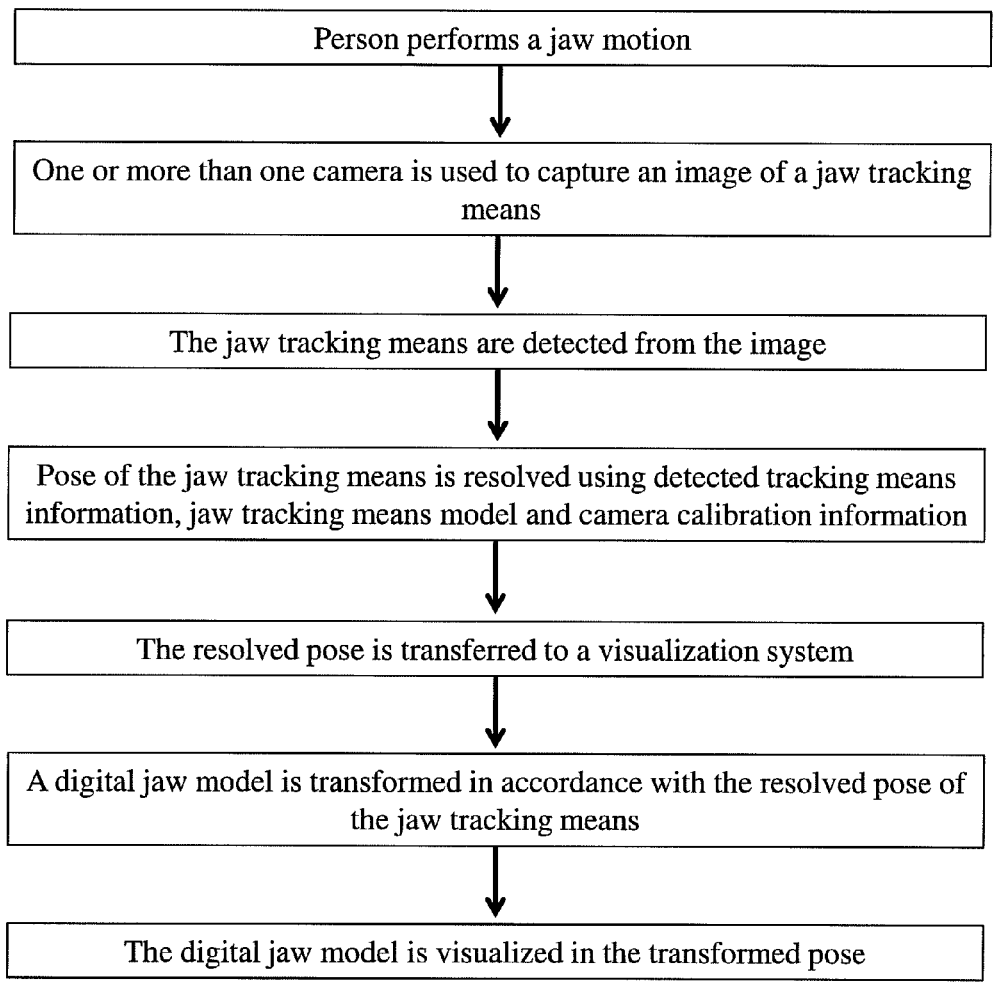
FIGS. 6 and 7 show procedures (by flow chart) applicable for use in the invention for generating a digital model visualizing jaw motion.

FIG. 6 shows one procedure applicable for use in the arrangement of the invention for visualizing jaw motion. When a person positioned for imaging by at least one camera arranged to a medical x-ray imaging apparatus starts jaw motion, tracking of the motion is initiated by taking photographs of at least one tracking item (in reference to the above, jaw tracking means comprise light reflecting reference object(s)). The control system of the arrangement then detects in a photograph said at least one tracking item and resolves its pose based on a reference model of the tracking item and camera calibration information. A modelled jaw movement can then be visualized on a display even in real time by repeatedly transforming the resolved pose of the tracking item to a digital model of the anatomy.

One method for producing the reference model of the tracking means includes first using the medical x-ray imaging apparatus for generating a CT reconstruction of a mandible and the tracking means including reference objects, and a visualization of that reconstruction is then presented on a display. When the user interface of the arrangement includes means to point locations of the reference objects on the displayed visualization, the image processing software of the arrangement is able to generate the reference model defining the spatial relationship between the reference objects and the reconstruction of the anatomy.

The camera calibration information referred to in FIG. 6 includes the intrinsic and extrinsic parameters of the one or more cameras of the arrangement. Such calibration information can be acquired using standard computer vision camera calibration methods known to those skilled in the art.

Figure 7:
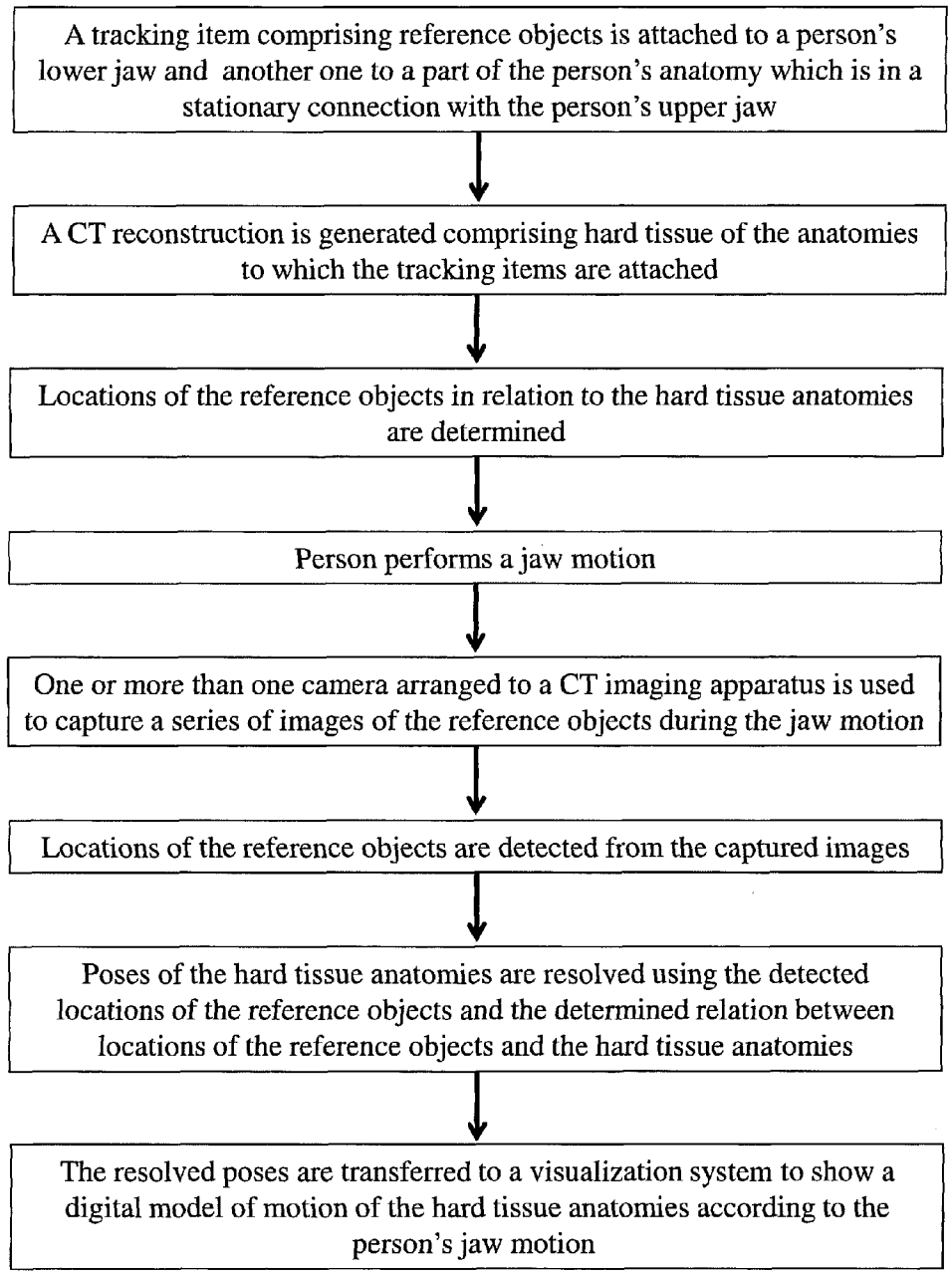

FIG. 7 shows another way of presenting an embodiment of the invention. According FIG. 7, a tracking item comprising reference objects is attached to a person's lower jaw and a second tracking item is attached to a part of the person's anatomy which is in a stationary connection with the person's upper jaw. Then, a CT reconstruction is generated comprising hard tissue of the anatomies to which the tracking items are attached and locations of the reference objects in relation to the hard tissue anatomies are determined. When a person performs a jaw motion, one or more than one camera arranged to a CT imaging apparatus is used to capture a series of images of the reference objects during the jaw motion and locations of the reference objects are detected from the captured images. Poses of the hard tissue anatomies are then resolved using the detected locations of the reference objects and the determined relation between locations of the reference objects and the hard tissue anatomies and the resolved poses are transferred to a visualization system to show a digital model of motion of hard tissue anatomies according to the person's jaw motion.

In summary, various aspects of the invention can be considered comprising tracking motion of a person's jaw by at least one camera configured to photograph movement of tracking items, the tracking items comprising reference objects and being attached to a person's lover jaw and to a person's upper jaw or to a part of the person's anatomy which is in a stationary connection with the upper jaw. An arrangement can be used comprising a control system including a first subsystem for controlling operations of the at least one camera to photograph the movement of the tracking items, and a second subsystem including image information processing means to detect projections and resolve poses of the tracking item in the images captured by the at least one camera and to apply this information to a digital model depicting hard tissue of at least the lower jaw and to generate a moving digital model to be shown on a display which visualizes movement of the hard tissue of the lower jaw according to the photographed movement of the reference objects. The arrangement can further comprise a medical x-ray imaging apparatus including an x-ray source and an x-ray image detector and the control system of the arrangement further comprise a third subsystem, the third subsystem including control functions relating to controlling operations of the medical x-ray imaging apparatus to acquire cranial x-ray image information and for generating a CT reconstruction of a cranial anatomy. The at least one camera to photograph the movement of the tracking items can be arranged to be a physical part of the medical x-ray imaging apparatus.

As to the medical x-ray apparatus, it can include a first structure carrying the x-ray source and the x-ray image detector and a second structure supporting the first structure. The at least one camera can be connected to either of the first structure and the second structure. Preferably, the arrangement includes two cameras arranged at a distance from each other on the first structure carrying said x-ray source and x-ray image detector. Further, the medical x-ray imaging apparatus can include a light source arranged at a close proximity of said at least one camera and the light source to be arranged to emit light essentially in a direction at which said at least one camera is aimed.

The display of the arrangement can be connected to structures of the medical x-ray imaging apparatus and the control system be configured to visualize on the display the digital model showing movement of the hard tissue according to said photographed movement detected by the at least one camera. Preferably, the control system is configured to visualize the movement of the digital model generated by the second subsystem essentially simultaneously while said first subsystem operates said at least one camera to photograph the movement of the reference objects. The digital model depicting hard tissue can be a visualization of a CT reconstruction of a person's jaw or jaws generated based on image data detected by the x-ray image detector of the medical x-ray imaging apparatus.

According to one embodiment, a user interface arranged in connection with the control system is configured to enable marking a feature of interest on the digital model depicting hard tissue and to include this marking in said moving digital model. The control system can further be configured to present on the display an image which is a visualization of a CT reconstruction of at least a part of the person's cranial anatomy together with a tracking item including reference objects attached to the person when image information for said reconstruction was acquired and, as a response to a user input indicating locations of the reference objects of said tracking item on said image, to generate a reference model defining a spatial relationship between said reference objects and the CT reconstruction.

The present disclosure advantageously combines an x-ray imaging apparatus with a camera system for tracking jaw motion physically arranged thereto. This improves the work flow of the imaging procedure and allows control of the CT apparatus and the motion tracking camera system by the same control system.

By arranging the jaw motion camera system to the x-ray imaging apparatus itself the present process provides the possibility to both generate a CT reconstruction which includes the anatomy and the tracking items (that is, scanning the anatomy while the tracking items are attached to a person) and to track jaw motion within the same procedure while a person is present and available for imaging at the x-ray imaging apparatus. Therefore, for one, no recalling of the person for imaging and no re-attaching of the tracking items is needed in case one notices any flaw in the process or problems in the image quality as the person is still present for any retake or performing additional jaw motions.

It will be apparent to one skilled in the art that as for its details, the present invention may be implemented also in other ways than according to the embodiments of the invention described above and that various details of the embodiments may be realized also in other combinations than ones literally discussed above. As an example, the medical x-ray imaging apparatus needs not to be exactly like the one shown in FIG. 1. The x-ray imaging means of the medical x-ray imaging apparatus may be arranged to, instead of a support arm, e.g. within a ring-shaped gantry.

The invention claimed is:

1. Arrangement for tracking motion of a person's jaw, the arrangement comprising:
   at least one camera configured to photograph movement of tracking items, the tracking items comprising reference objects and being attached to a person's lower jaw and to a person's upper jaw or to a part of the person's anatomy which is in a stationary connection with the upper jaw;
   a control system including a first subsystem for controlling operations of said at least one camera to photograph said movement of the tracking items, and
   a second subsystem including image information processing means to detect projections and resolve poses of the tracking item in the images captured by said at least one camera and to apply this information to a digital model depicting hard tissue of at least the lower jaw and to generate a moving digital model to be shown on a display which visualizes movement of the hard tissue of the lower jaw according to said photographed movement of the reference objects;
   wherein the arrangement further comprises
   a medical x-ray imaging apparatus including an x-ray source and an x-ray image detector and
   the control system further comprises a third subsystem, the third subsystem including control functions relating to controlling operations of said medical x-ray imaging apparatus to acquire cranial x-ray image information and for generating a CT reconstruction of a cranial anatomy, characterized in that
   said at least one camera arranged to photograph said movement of the tracking items is a physical part of said medical x-ray imaging apparatus.

2. Arrangement according to claim 1, wherein said medical x-ray apparatus includes a first structure carrying said x-ray source and x-ray image detector and a second structure supporting the first structure, and wherein said at least one camera is connected to either of the first structure and the second structure.

3. Arrangement according to claim 2, wherein the arrangement includes two cameras arranged at a distance from each other to said first structure carrying said x-ray source and x-ray image detector.

4. Arrangement according to claim 2, wherein said first structure is a rotatable arm upon which the x-ray source and the x-ray image detector are arranged at a distance from each other and wherein said at least one camera is arranged on said rotatable arm adjacent said x-ray image detector.

5. Arrangement according to claim 1, wherein said medical x-ray imaging apparatus includes a light source arranged at a close proximity of said at least one camera and said light source is arranged to emit light essentially in a direction at which said at least one camera is aimed.

6. Arrangement according to claim 1, wherein said display is connected to structures of the medical x-ray imaging apparatus and said control system is configured to visualize on the display said digital model showing movement of the hard tissue according to said photographed movement detected by said at least one camera.

7. Arrangement according to claim 1, wherein the control system is configured to visualize said movement of the digital model generated by said second subsystem essentially simultaneously while said first subsystem operates said at least one camera to photograph the movement of the reference objects.

8. Arrangement according to claim 1, wherein said digital model depicting hard tissue is a visualization of a CT reconstruction of a person's jaw or jaws generated based on image data detected by the x-ray image detector of said medical x-ray imaging apparatus.

9. Arrangement according to claim 1 further comprising a user interface in connection with said control system, wherein the user interface is configured to enable marking a feature of interest on said digital model depicting hard tissue and wherein the control system is configured to include this marking in said moving digital model.

10. Arrangement according to claims 1, wherein the control system is configured to present on said display an image which is a visualization of a CT reconstruction of at least a part of the person's cranial anatomy together with a tracking item including reference objects attached to the person when image information for said reconstruction was acquired and, as a response to a user input indicating locations of the reference objects of said tracking item on said image, to generate a reference model defining a spatial relationship between said reference objects and the CT reconstruction.

11. Arrangement according to claim 1, wherein the reference objects are light reflecting.

12. Method for tracking motion of a person's jaw, comprising:

attaching a first tracking item comprising reference objects to a person's lower jaw and a second tracking item comprising reference objects to a part of the person's anatomy which is in a stationary connection with the person's upper jaw;
generating a CT reconstruction comprising hard tissue of the anatomies to which the tracking items are attached;
determining locations of the reference objects in relation to the hard tissue anatomies;
capturing a series of images of the reference objects while a person performs jaw motion;
detecting locations of the reference objects from the captured images;
resolving poses of the hard tissue anatomies using the detected locations of the reference objects and the determined relation between locations of the reference objects and the hard tissue anatomies;
transferring the resolved poses to a visualization system to show a digital model of motion of the hard tissue anatomies according to the person's jaw motion; characterized in that
said series of images is captured by at least one camera arranged to a CT imaging apparatus.

13. Method according to claim 12, wherein said motion of the digital model of the hard tissue anatomies is visualized essentially simultaneously while said at least one camera captures said images.

14. Method according to claim 12, wherein said second tracking item is connected to the patient's forehead.

15. Method according to claim 12, wherein said hard tissue anatomy comprises cranial hard tissue.

16. Method according to claim 12, wherein said at least camera and a light source are disposed on a rotating arm of a CT imaging apparatus.

17. Method according to claim 16, further comprising illuminating the reference objects of the first and the second tracking item by said light source during capturing of the images.

18. Method according to claim 12, further comprising marking locations of reference objects on said CT reconstruction using a user interface and depicting said locations on the images.

19. Method according to claim 12, wherein at least one tracking item includes at least 5 light reflecting objects spaced apart from each other.

* * * * *